US008687003B2

(12) United States Patent
Dalesch et al.

(10) Patent No.: US 8,687,003 B2
(45) Date of Patent: Apr. 1, 2014

(54) METHODS AND APPARATUS FOR DISPLAYING FLOW RATE GRAPHS AND ALARMS ON A DIALYSIS SYSTEM

(75) Inventors: Charles Dalesch, Palm Harbor, FL (US); Alex Reidiboim, Toronto (CA); Gabriel Gutierrez, Don Mills (CA); Kiril Vasilev, Oakville (CA); Cristina Illiescu, Vaughan (CA); William Joseph Thomas, Tarpon Springs, FL (US); David H. Hoffmiester, Grayslake, IL (US); Ashok Darisipudi, Bartlett, IL (US); Deanna N. Pilling, Palatine, IL (US); Philip Pupa, Libertyville, IL (US)

(73) Assignees: Baxter International Inc., Deerfield, IL (US); Baxter Healthcare S.A., Glattpark (Opfikon) (CH)

( * ) Notice: Subject to any disclaimer, the term of this patent is extended or adjusted under 35 U.S.C. 154(b) by 333 days.

(21) Appl. No.: 12/853,058

(22) Filed: Aug. 9, 2010
(Under 37 CFR 1.47)

(65) Prior Publication Data
US 2011/0169834 A1 Jul. 14, 2011

Related U.S. Application Data

(63) Continuation of application No. 12/639,449, filed on Dec. 16, 2009, now abandoned.

(51) Int. Cl.
*G06T 11/20* (2006.01)

(52) U.S. Cl.
USPC .......................................................... 345/440

(58) Field of Classification Search
None
See application file for complete search history.

(56) References Cited

U.S. PATENT DOCUMENTS

| | | |
|---|---|---|
| 4,096,859 A | 6/1978 | Agarwal et al. |
| RE31,302 E | 7/1983 | Stambler |
| 4,428,381 A | 1/1984 | Hepp |
| 4,990,258 A | 2/1991 | Bjare et al. |
| 5,265,010 A | 11/1993 | Evans-Paganelli et al. |
| 5,267,314 A | 11/1993 | Stambler |
| 5,276,611 A | 1/1994 | Ghiraldi |
| 5,352,364 A | 10/1994 | Kruger et al. |
| 5,401,238 A | 3/1995 | Pirazzoli |
| 5,486,999 A | 1/1996 | Mebane |
| 5,517,405 A | 5/1996 | McAndrew et al. |
| 5,524,073 A | 6/1996 | Stambler |
| 5,555,303 A | 9/1996 | Stambler |
| 5,558,638 A | 9/1996 | Evers et al. |
| 5,609,770 A | 3/1997 | Zimmerman et al. |
| 5,618,441 A | 4/1997 | Rosa et al. |
| 5,620,608 A | 4/1997 | Rosa et al. |
| 5,643,201 A | 7/1997 | Peabody et al. |
| 5,646,998 A | 7/1997 | Stambler |
| 5,664,109 A | 9/1997 | Johnson et al. |

(Continued)

FOREIGN PATENT DOCUMENTS

| | | |
|---|---|---|
| WO | WO02/07796 | 1/2002 |
| WO | WO02/07797 | 1/2002 |

*Primary Examiner* — Edward Martello
(74) *Attorney, Agent, or Firm* — K&L Gates LLP

(57) ABSTRACT

The present disclosure provides methods and apparatus for displaying flow rate graphs and alarms on a dialysis system. The disclosed methods and apparatus allow a user to simultaneously view a normal flow rate graph, one or more abnormal flow rate graphs, an actual flow rate graph, and an alarm type. Preferably, the three graphs are at the same scale and time-aligned so the user can quickly diagnose issues associated with drain and catheter problems.

39 Claims, 3 Drawing Sheets

(56) References Cited

U.S. PATENT DOCUMENTS

| | | |
|---|---|---|
| 5,672,154 A | 9/1997 | Sillen et al. |
| 5,687,716 A | 11/1997 | Kaufmann et al. |
| 5,713,350 A | 2/1998 | Yokota et al. |
| 5,737,539 A | 4/1998 | Edelson et al. |
| 5,744,027 A | 4/1998 | Connell et al. |
| 5,758,095 A | 5/1998 | Albaum et al. |
| 5,772,585 A | 6/1998 | Lavin et al. |
| 5,777,598 A * | 7/1998 | Gowda et al. .................. 345/440 |
| 5,785,650 A | 7/1998 | Akasaka et al. |
| 5,788,851 A | 8/1998 | Kenley et al. |
| 5,793,302 A | 8/1998 | Stambler |
| 5,823,949 A | 10/1998 | Goltra |
| 5,832,448 A | 11/1998 | Brown |
| 5,833,599 A | 11/1998 | Schrier et al. |
| 5,845,253 A | 12/1998 | Rensimer et al. |
| 5,845,255 A | 12/1998 | Mayaud |
| 5,857,967 A | 1/1999 | Frid et al. |
| 5,879,163 A | 3/1999 | Brown et al. |
| 5,883,370 A | 3/1999 | Walker et al. |
| 5,897,493 A | 4/1999 | Brown |
| 5,899,855 A | 5/1999 | Brown |
| 5,911,133 A | 6/1999 | Soble |
| 5,918,603 A | 7/1999 | Brown |
| 5,924,074 A | 7/1999 | Evans |
| 5,933,136 A | 8/1999 | Brown |
| 5,936,541 A | 8/1999 | Stambler |
| 5,937,387 A | 8/1999 | Summerell et al. |
| 5,938,938 A | 8/1999 | Bosetto et al. |
| 5,951,300 A | 9/1999 | Brown |
| 5,959,529 A | 9/1999 | Kail, IV |
| 5,960,403 A | 9/1999 | Brown |
| 5,964,700 A | 10/1999 | Tallman et al. |
| 5,974,148 A | 10/1999 | Stambler |
| 5,974,389 A | 10/1999 | Clark et al. |
| 5,987,519 A | 11/1999 | Peifer et al. |
| 5,991,731 A | 11/1999 | Colon et al. |
| 5,997,476 A | 12/1999 | Brown |
| 6,014,626 A | 1/2000 | Cohen |
| 6,014,631 A | 1/2000 | Teagarden et al. |
| 6,024,699 A | 2/2000 | Surwit et al. |
| 6,026,363 A | 2/2000 | Shepard |
| 6,032,119 A | 2/2000 | Brown et al. |
| 6,050,940 A | 4/2000 | Braun et al. |
| 6,067,524 A | 5/2000 | Byerly et al. |
| 6,074,345 A | 6/2000 | van Oostrom et al. |
| 6,076,166 A | 6/2000 | Moshfeghi et al. |
| 6,081,809 A | 6/2000 | Kumagai |
| 6,101,478 A | 8/2000 | Brown |
| 6,104,626 A | 8/2000 | Katakura et al. |
| 6,108,635 A | 8/2000 | Herren et al. |
| 6,112,224 A | 8/2000 | Peifer et al. |
| 6,122,351 A | 9/2000 | Schlueter, Jr. et al. |
| 6,154,726 A | 11/2000 | Rensimer et al. |
| 6,154,750 A | 11/2000 | Roberge et al. |
| 6,157,914 A | 12/2000 | Seto et al. |
| 6,168,563 B1 | 1/2001 | Brown |
| 6,171,237 B1 | 1/2001 | Avitall et al. |
| 6,177,940 B1 | 1/2001 | Bond et al. |
| 6,188,407 B1 | 2/2001 | Smith et al. |
| 6,192,345 B1 | 2/2001 | Chicorel |
| 6,212,424 B1 | 4/2001 | Robinson |
| 6,213,942 B1 | 4/2001 | Flach et al. |
| 6,230,142 B1 | 5/2001 | Benigno et al. |
| 6,234,964 B1 | 5/2001 | Iliff |
| 6,246,992 B1 | 6/2001 | Brown |
| 6,263,330 B1 | 7/2001 | Bessette |
| 6,269,339 B1 | 7/2001 | Silver |
| 6,272,470 B1 | 8/2001 | Teshima |
| 6,277,071 B1 | 8/2001 | Hennessy et al. |
| 6,278,999 B1 | 8/2001 | Knapp |
| 6,280,634 B1 | 8/2001 | Shah et al. |
| 6,284,131 B1 | 9/2001 | Hogard et al. |
| 6,289,316 B1 | 9/2001 | Aghili et al. |
| 6,292,783 B1 | 9/2001 | Rohler et al. |
| 6,308,171 B1 | 10/2001 | De La Huerga |
| 6,311,163 B1 | 10/2001 | Sheehan et al. |
| 6,312,378 B1 | 11/2001 | Bardy |
| 6,314,405 B1 | 11/2001 | Richardson |
| 6,315,720 B1 | 11/2001 | Williams et al. |
| 6,317,719 B1 | 11/2001 | Schrier et al. |
| 6,322,502 B1 | 11/2001 | Schoenberg et al. |
| 6,336,900 B1 | 1/2002 | Alleckson et al. |
| 6,345,268 B1 | 2/2002 | De La Huerga |
| 6,347,329 B1 | 2/2002 | Evans |
| 6,358,203 B2 | 3/2002 | Bardy |
| 6,364,834 B1 | 4/2002 | Reuss et al. |
| 6,368,273 B1 | 4/2002 | Brown |
| 6,375,614 B1 | 4/2002 | Braun et al. |
| 6,385,589 B1 | 5/2002 | Trusheim et al. |
| 6,402,691 B1 | 6/2002 | Peddicord et al. |
| 6,406,426 B1 | 6/2002 | Reuss et al. |
| 6,409,662 B1 | 6/2002 | Lloyd et al. |
| 6,416,471 B1 | 7/2002 | Kumar et al. |
| 6,434,531 B1 | 8/2002 | Lancelot et al. |
| 7,033,539 B2 | 4/2006 | Krensky et al. |
| 7,297,129 B2 * | 11/2007 | Kinouchi et al. ............ 604/4.01 |
| 7,750,908 B2 * | 7/2010 | Kincaid et al. ................. 345/440 |
| 2001/0034614 A1 | 10/2001 | Fletcher-Haynes et al. |
| 2002/0040282 A1 | 4/2002 | Bailey et al. |
| 2002/0082728 A1 | 6/2002 | Mueller et al. |
| 2002/0087361 A1 | 7/2002 | Benigno et al. |
| 2002/0128861 A1 | 9/2002 | Lau et al. |
| 2002/0128862 A1 | 9/2002 | Lau et al. |
| 2002/0132214 A1 | 9/2002 | Mattson et al. |
| 2002/0133376 A1 | 9/2002 | Fritschen et al. |
| 2002/0162778 A1 | 11/2002 | Peabody et al. |
| 2003/0083901 A1 | 5/2003 | Bosch et al. |
| 2004/0010421 A1 | 1/2004 | Mina et al. |
| 2005/0102165 A1 * | 5/2005 | Oshita et al. ..................... 705/3 |
| 2006/0126669 A1 * | 6/2006 | Beronja ..................... 370/503 |
| 2006/0289342 A1 * | 12/2006 | Sugioka et al. ................. 210/85 |
| 2007/0109301 A1 * | 5/2007 | Smith ......................... 345/440 |
| 2007/0138069 A1 * | 6/2007 | Roncadi et al. ............. 210/96.2 |
| 2009/0231341 A1 * | 9/2009 | Lord et al. ................... 345/440 |
| 2010/0083164 A1 * | 4/2010 | Martin et al. ................. 715/781 |

* cited by examiner

METHODS AND APPARATUS FOR DISPLAYING FLOW RATE GRAPHS AND ALARMS ON A DIALYSIS SYSTEM

PRIORITY CLAIM

This continuation application claims priority to and the benefit of U.S. application Ser. No. 12/639,449, filed Dec. 16, 2009 (now abandoned), the entirety of which is incorporated herein.

TECHNICAL FIELD

The present application relates in general to dialysis systems and more specifically to methods and apparatus for displaying flow rate graphs and alarms on a dialysis system.

BACKGROUND

Due to disease, insult or other causes, a person's renal system can fail. In renal failure of any cause, there are several physiological derangements. The balance of water, minerals and the excretion of daily metabolic load is no longer possible in renal failure. During renal failure, toxic end products of nitrogen metabolism (urea, creatinine, uric acid, and others) can accumulate in blood and tissues.

Kidney failure and reduced kidney function have been treated with dialysis. Dialysis removes waste, toxins and excess water from the body that would otherwise have been removed by normal functioning kidneys. Dialysis treatment for replacement of kidney functions is critical to many people because the treatment is life saving. One who has failed kidneys could not continue to live without replacing at least the filtration functions of the kidneys.

Hemodialysis and peritoneal dialysis are two types of dialysis therapies commonly used to treat loss of kidney function. Hemodialysis treatment utilizes the patient's blood to remove waste, toxins and excess water from the patient. The patient is connected to a hemodialysis machine and the patient's blood is pumped through the machine. Catheters are inserted into the patient's veins and arteries to connect the blood flow to and from the hemodialysis machine. As blood passes through a dialyzer in the hemodialysis machine, the dialyzer removes the waste, toxins and excess water from the patient's blood and returns the blood back to the patient. A large amount of dialysate, for example about 120 liters, is used to dialyze the blood during a single hemodialysis therapy. The spent dialysate is then discarded. Hemodialysis treatment lasts several hours and is generally performed in a treatment center about three or four times per week.

Peritoneal dialysis utilizes a dialysis solution or "dialysate," which is infused into a patient's peritoneal cavity through a catheter implanted in the cavity. The dialysate contacts the patient's peritoneal membrane in the peritoneal cavity. Waste, toxins and excess water pass from the patient's bloodstream through the peritoneal membrane and into the dialysate. The transfer of waste, toxins, and water from the bloodstream into the dialysate occurs due to diffusion and osmosis, i.e., an osmotic gradient occurs across the membrane. The spent dialysate drains from the patient's peritoneal cavity and removes the waste, toxins and excess water from the patient. This cycle is repeated.

However, continuing needs exist to provide improved dialysis systems. For example, needs exist to provide simplified dialysis systems that are easier for patients to use and operate. In particular, a need exits for an improved display of flow rate graphs and alarms on dialysis systems to ease diagnosis of problems during dialysis such as catheter occlusion problems, blocked catheters, occurrences of peritonitis or constipation, etc.

SUMMARY

The present disclosure provides methods and apparatus for displaying flow rate graphs and alarms on a dialysis system. The disclosed methods and apparatus allow a user to simultaneously view a normal flow rate graph, one or more abnormal flow rate graphs, an actual flow rate graph, and an alarm type. Preferably, the three graphs are at the same scale and time-aligned so the user can quickly diagnose issues associated with drain and catheter problems.

DETAILED DESCRIPTION

Figure 1:
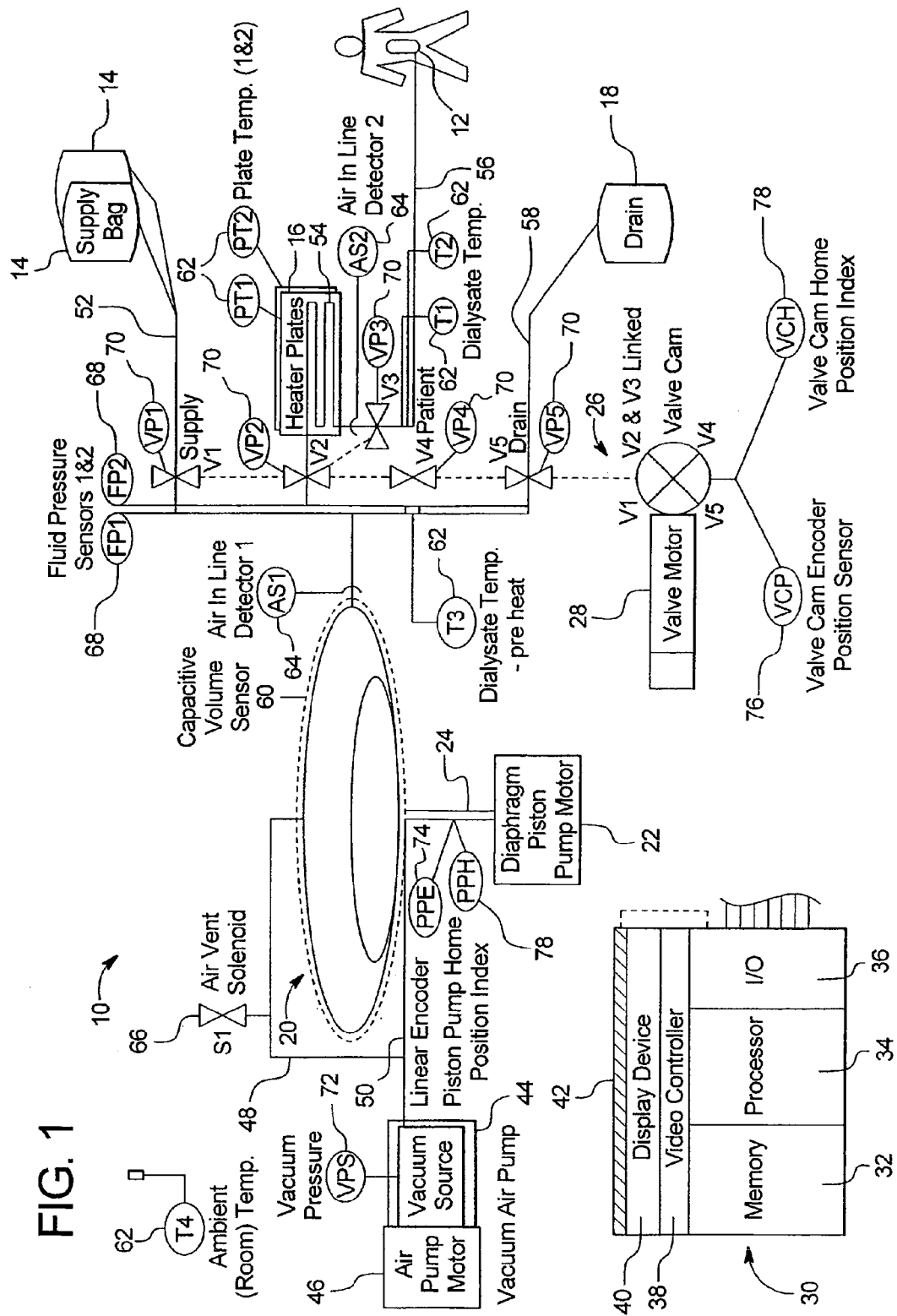
FIG. 1 is a block diagram of an example dialysis system.

Referring now to the drawings and in particular to FIG. 1, a typical therapy performed by the system 10 of the present system begins by draining dialysis solution that is already in the patient's peritoneal cavity 12. The system 10 pumps fresh dialysate from one of a plurality of supply bags 14, through an in-line heater 16 to the patient or peritoneal cavity 12. After a dwell period in the peritoneal cavity 12, the spent dialysate in the cavity is pumped out of the patient or cavity 12 to a drain 18 or other disposal means. The system 10 then pumps fresh dialysate from the supply bags 14 to the patient or peritoneal cavity 12 and the procedure is repeated as defined in the therapy protocol. The system 10 in an embodiment pumps a last bag of dialysate (usually, a dialysate having a different formulation than the dialysate in the other supply bags) to the peritoneal cavity 12 for an extended dwell, such as a daytime dwell.

In an embodiment, the system 10 includes a mechanically operated diaphragm pump 20. The mechanically operated diaphragm pump 20 employs a pump motor 22 and a linear pump actuator 24. A vacuum may also be used with the mechanical actuator for the diaphragm pump 20. In another embodiment, the pump is completely fluidly activated.

In FIG. 1 the system 10 also includes a valve actuator 26, which mechanically actuates valves V1 to V5. A controller 30 controls the valve actuator 26 to open valves V1 to V5 as necessary to achieve the desired direction of dialysate fluid flow. In an embodiment, the valve actuator 26 includes a valve motor 28 and a camshaft, which opens one or more of the valves V1 to V5 to achieve the desired dialysate flow.

The controller 30 includes a plurality of processors and a memory device for each processor. The processors include a main microprocessor and a number of delegate processors. The main microprocessor runs certain higher level tasks such as the graphical user interface ("GUI") described below. The delegate processors perform lower level tasks, such as moving valves, reading sensors, controlling heater duty cycle, etc. An additional processor is provided solely for the purpose of tracking safety parameters, such as heater plate and medical fluid temperature. For purposes of the present system, except where otherwise specified, the term "processor 34" refers collectively to all of the processors and the term "memory device 32" refers collectively to all of the corresponding memory devices.

The controller 30 also includes an input/output ("I/O") module 36. The device memory device 32 stores a computer program that contains a step by step sequence for the system 10 and configures certain outputs to occur upon specified inputs. The processor 34 runs the program in the memory 32. The I/O module 36 accepts signal lines from various sensors. The I/O module 36 also connects to power lines including input power lines (including if battery powered) and power lines outputted to the various electrical components.

The controller 30, in an embodiment, includes a video controller 38, which may be a video card. The controller 30 also includes a display device or video monitor 40 that displays medical treatment or dialysis information to a patient or operator. In an embodiment, the controller 30 further includes a touch screen 42 that interfaces with the video monitor 40 and electrically communicates with the I/O module 36. The touch screen 42 enables the patient or operator to input medical treatment or dialysis information into the controller 30.

The controller 30 controls the heater 16, the pump 20 and the valve actuator 26 in a number of different phases that make up a single medical or dialysis treatment. In a first pump fill phase, controller 30 activates the pump 20 to pump medical fluid or dialysate from one of the supply bags 14. In FIG. 1, the controller 30 commands a vacuum source 44, including an air pump motor 46, to pull a vacuum on both sides of the pump 20 through a first vacuum line 48 and a second vacuum line 50. The vacuum lines 48 and 50 pull respective vacuums through first and second pump chamber walls to suction one of a pair of opposing membranes inside the pump chamber against the interior of the pump chamber. The other membrane is held against a piston head in the pump 20. The other membrane alternatively temporarily or permanently mechanically attaches to the piston head, rendering the vacuum on the piston side of the pump 20 unnecessary.

With the membranes maintained against the interior of the pump chamber and the piston head, the controller 30 commands the linear actuator 24 to withdraw within the pump 20. The withdrawal causes the membranes inside the pump chamber to pull further apart. At this time, the controller 30 controls the valve actuator 26 so that only valve V1 is open. The pulling apart of the membranes causes a negative pressure to occur in fill line 52, wherein the negative pressure pulls medical fluid or dialysate from the supply bag 14, through the fill line 52, into a receptacle created by the opened membranes inside the pump chamber of pump 20.

In a patient fill phase, with the negative pressure still maintained by the vacuum source 44, through the pump chamber walls, on the interior membranes, the controller 30 causes the linear pump actuator 24 to move upwards within the pump 20. The upward movement of the actuator 24 and an attached piston head provides a positive mechanical pressure that closes the membrane receptacle and thereby pumps the medical fluid out of the pump 20. At this time, the controller 30 controls the valve actuator 26 so that only valves V2 and V3 are open. Consequently, all of the fluid exiting pump 20 is pumped through a heater line 54, past the in-line heater 16, through a catheter line 56, and into the patient, for example, the patient's peritoneal cavity 12. The catheter line 56 in an embodiment connects to a single lumen catheter, which is implanted into the patient 12. Although, in other embodiments, the system 10 can employ a multi-lumen catheter.

The heater 16 in an embodiment includes one or more electrical heating plates, which heat the medical fluid to roughly body temperature. The controller 30 energizes and de-energizes the heater 16 as necessary to obtain the proper fluid temperature. The controller 30 can close valves V2 and V3, located on opposing sides of the heater 16 in the heater line 54, if the medical fluid is too hot or too cold. The improperly heated dialysate does not enter the peritoneal cavity 12.

The controller 20 repeats the pump fill phase and the heater fill phase until the patient's the peritoneal cavity 12 becomes full of fluid according to the therapy protocol. In an embodiment, the volume inside the pump is about thirty to fifty milliliters, and an adult patient typically uses about two liters of dialysis fluid. Accordingly, the pump fill phase and the heater fill phase can be repeated on the order of fifty times. In an embodiment, the pump actuator 24 maintains a fluid pressure at the pump 20 of about three pounds per square inch ("psi").

The system 10 provides a fluid volume sensor 60, which measures the actual volume of medical fluid that has been forced through the pump 20. By summing multiple individual pump volumes, the controller accurately knows how much medical fluid or dialysate has been delivered to the patient 12. The system 10 in an embodiment repeats the pump fill phase and the heater fill phase until the pump 20 has delivered a predetermined volume of medical fluid. The predetermined volume can be inputted into the controller 30 by a patient or operator via the touch screen 42.

In a dwell phase, the controller 30 lets the medical fluid or dialysate remain within the patient 12 for an amount of time, which can be controlled by the controller 30, the patient 12 or an operator. In an embodiment, the controller 30 determines the dwell time, but the patient 12 or operator can override the system 10 and command that the system 10 remove the medical fluid from the patient 12.

In a second pump fill phase, the medical fluid is removed from the patient 12. The controller 30 and the actuator 26 open valve V4, while shutting the remaining valves. With the vacuum source still maintaining a negative pressure on the membranes inside the pump 20, the linear actuator 24 withdraws the pump piston within the chamber of pump 20 and reopens the receptacle between the membranes. The negative pressure created by the opening receptacle pulls the medical fluid from the patient 12, through the catheter line 56 and into the membrane receptacle formed inside the pump 20.

In a drain phase, with the negative pressure still maintained by the vacuum source 44, through the pump chamber walls, on the interior membranes, the controller 30 causes the linear pump actuator 24 to move upwardly within the pump 20. The upward movement of the actuator 24 causes a positive mechanical pressure to close the membrane receptacle and thereby pump the medical fluid out of the pump 20. At this time, the controller 30 controls the valve actuator 26 so that only valve V5 is open. Consequently, all of the fluid exiting pump 20 is pumped through a drain line 58 and into the drain 18. Drain 18 can be a drain bag or a drain pipe inside a home, a hospital or elsewhere.

The system 10 includes temperature sensors 62, such as the sensors T1 to T4, which measure the temperature at relevant places within the system 10. In an embodiment, the sensors 62 are non-invasive, however, any other types of temperature sensors may be employed. As illustrated in FIG. 1, sensors T1 and T2 provide redundant post heater feedback of the fluid temperature to the controller 30. Sensor T3 provides a temperature of the medical fluid prior to heating. Sensor T4 provides the ambient temperature.

The system 10 also provides temperature sensors 62 that monitor the temperature of the heater 16. In an embodiment, the heater 16 is an in-line plate heater. The in-line plate heater 16 can have one or more heater plates, for example, two heater plates having a disposable unit placed between same. Separate temperature sensors PT1 and PT2 are provided to monitor the temperature of each of the plates of the plate heater. The system 10 can thereby control each plate heater individually.

The system 10 includes one or more air sensors 64, such as the sensor AS1, placed directly at the throat of the inlet and outlet of the pump 20. Another air sensor AS2 monitors air in the medical fluid after it leaves the heater 16 and just before the final shut-off valve V3 leading to the catheter line 56. The controller 30 monitors the air content sensed by the air sensors 64 and thereby controls the system 10 to perform any necessary air purge. The system 10 can separate and discharge the air from the fluid or simply convey the air to the drain 18. The system 10 also includes an air vent solenoid 66, which is operated by the controller 30. The air vent solenoid 66 enables the system 10 to relieve the vacuum applied to one or both of the membranes in the pump 20.

The system 10 can accumulate air for various reasons. For example, the valves V1 to V5 and fluid lines, such as lines 52, 54, 56 and 58 may contain air prior to priming the system 10. The supply bags 14 may also introduce air into the pump 20. The patient 12 can also produce certain gasses, which become entrained in the dialysate and enter the pump 20. Further, if minor leaks exist in the fluid disposable or the connections to the supply bag 14, the catheter at the patient 12, or the drain bag, the pump 20 can draw air in through the leaks.

The system 10 provides various fluid pressure sensors 68. Fluid pressure sensors FP1 and FP2 provide a redundant pressure reading of the fluid in the fill line 52 leading to the pump 60. The fluid pressure sensors 68 provide a signal to the controller 30 that indicates the respective fluid pressure at that location. Based on the signals from the pressure sensors FP1 and FP2, the controller 30 operates the fluid pumps and valves to obtain and maintain a desired fluid pressure. As stated above, the system 10 maintains the pump pressure, for example, at about three psi.

The system 10 also provides various valve pressure sensors 70. Valve pressure sensors VP1 to VP5 detect the fluid pressure at the valves V1 to V5. The system 10 further provides one or more vacuum pressure sensors 72, for example, at the vacuum source 44, to ensure that a proper vacuum is maintained on the membrane receptacle within the pump 20.

In an embodiment, the fluid pressure, valve pressure and vacuum sensors 68, 70 and 72, respectively, are non-invasive sensors. That is, the sensors do not physically contact (and possibly contaminate) the medical fluid or dialysate. Of course, the system 10 can include other flow and pressure devices, such as flow rate sensors, pressure gauges, flowmeters, or pressure regulators in any suitable quantity and at any desired location.

The system 10 also includes various positioning sensors. In an embodiment, the positioning sensors include a linear encoder 74 that monitors the position of the linear pump actuator 24 and a rotary encoder 76 that monitors the angular position of the valve actuator 26 or camshaft. An encoder is one type of positioning feedback device that can be employed. Other types of positioning feedback systems include proximity sensors and magnetic pick-ups that sense a pulse, e.g., a gear tooth of a gear attached to the camshaft, and output the pulse to a counter or microprocessor.

The encoders 74 and 76 also typically provide a pulsed output, which is sent to the controller 30. The pulsed output tells the controller 30 how many steps or how far the linear pump actuator 24 or the valve actuator 26 is from a home position or home index 78. For example, the home position 78 can be the pump fully open or pump fully closed position for the linear encoder 74 and the zero degree position for the rotary encoder 76.

In an embodiment, the encoders 74 and 76 are absolute type encoders that know the location of the home position 78 even after a power loss. In another embodiment, the encoders 74 and 76 are incremental encoders and a battery back-up is provided to the controller so that the system 10 can maintain the location of the home position 78 even when no external power is applied. Further alternatively, system 10 can be programmed to automatically move the pump actuator 24 and the valve actuator 26 upon power-up until a home position is sensed, wherein the system 10 can begin to run the main sequence.

During the operation of the system 10 an event may occur that requires high priority information to be displayed to the operator, for example, an alarm and corresponding message either on the display device 40 or on a separate dedicated alarm display. Example problems that may generate an alarm include catheter occlusion problems, blocked catheters, occurrences of peritonitis or constipation, etc.

Figure 2:
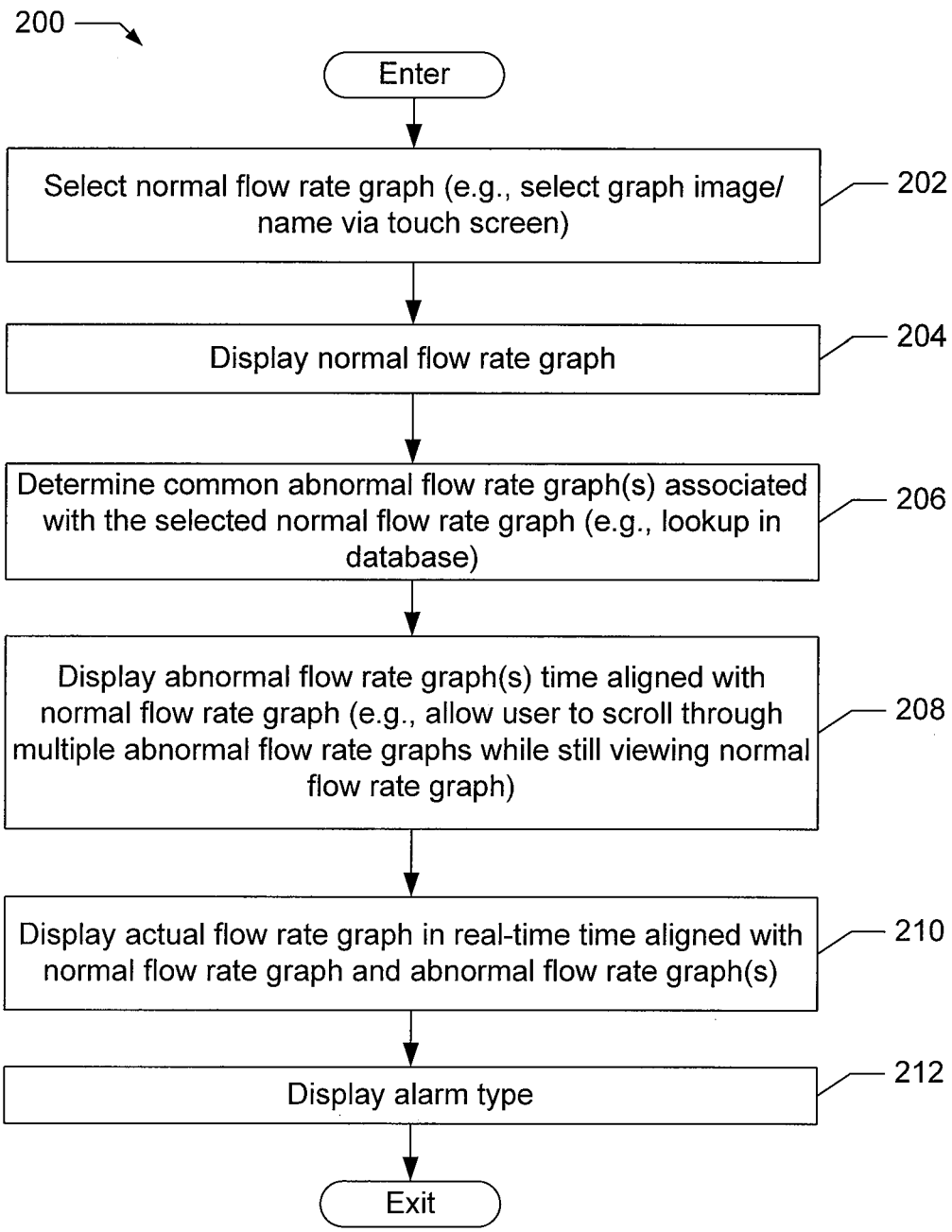
FIG. 2 is a flowchart showing an example process for displaying flow rate graphs and alarms on a dialysis system.

A flowchart of an example process 200 for displaying flow rate graphs and alarms on a dialysis system is presented in FIG. 2. Preferably, the process 200 is embodied in one or more software programs which are stored in one or more memories and executed by one or more processors. Although the process 200 is described with reference to the flowchart illustrated in FIG. 2, it will be appreciated that many other methods of performing the acts associated with process 200 may be used. For example, the order of many of the steps may be changed, some of the steps described may be optional, and additional steps may be included.

Figure 3:
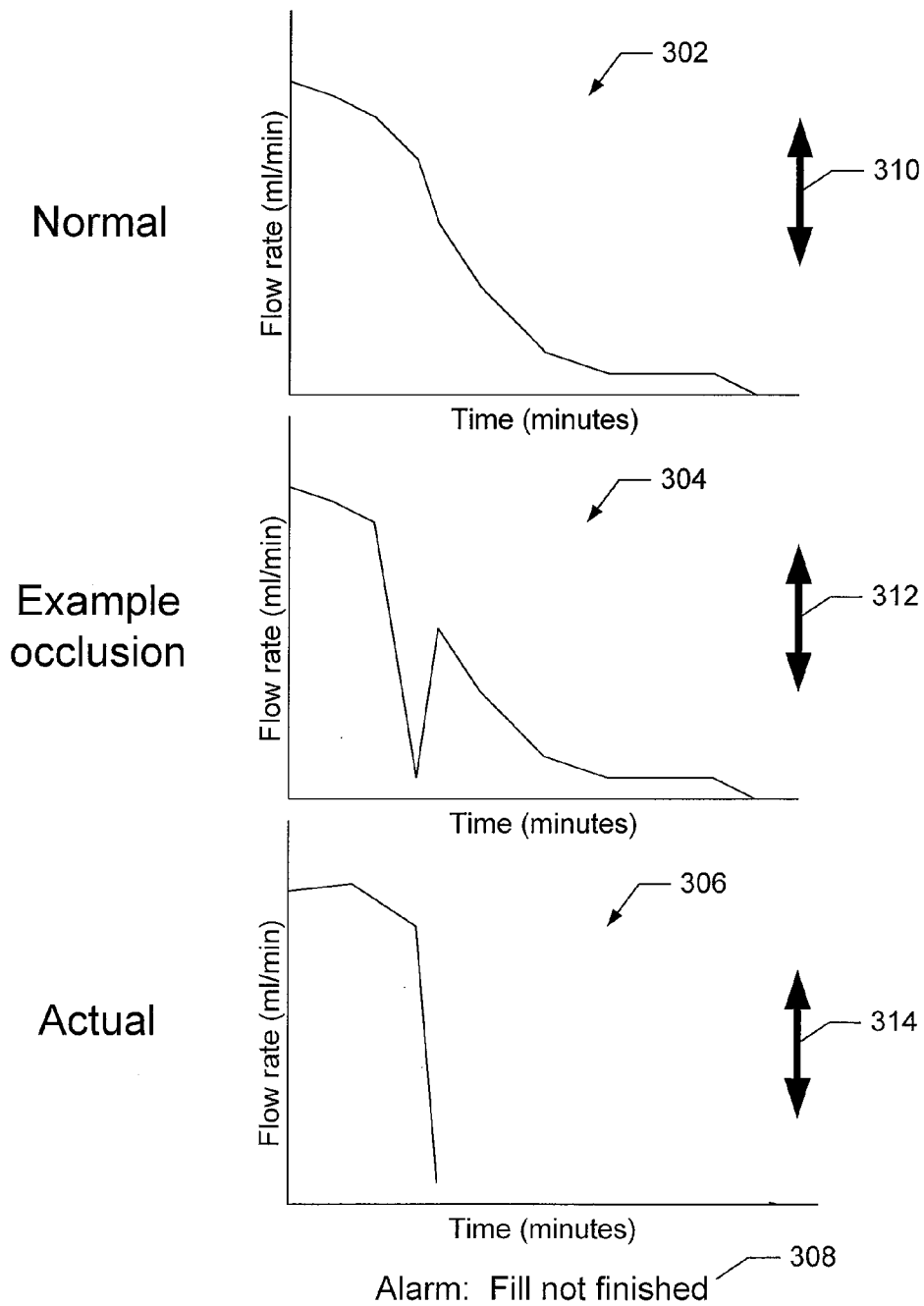
FIG. 3 is a screen shot of an example user interface for simultaneously displaying a normal flow rate graph, one or more abnormal flow rate graphs, an actual flow rate graph, and an alarm type.

In general, and as shown in FIG. 3, the process 200 allows a user to simultaneously view a normal flow rate graph 302, one or more abnormal flow rate graphs 304, an actual flow rate graph 306, and an alarm type 308. Preferably, the three graphs are at the same scale and time-aligned so the user can quickly diagnose issues associated with drain and catheter problems.

More specifically, the process 200 begins when the user selects a normal flow rate graph 302 (block 202). The normal flow rate graph 302 represents the physician's intended flow rate for the patient based on the patient's age, weight, etc. For example, the user may scroll through various normal flow rate graphs by selecting an arrow button 310. Alternatively, the user may select the normal flow rate graph 302 by touching an image and/or name of the normal flow rate graph 302 on a touch screen 42. Once selected, the normal flow rate graph 302 is displayed (block 204).

Based on the selected flow rate graph 302, the system 10 determines one or more common abnormal flow rate graphs 304 associated with the selected normal flow rate graph 302 (block 206). For example, the system 10 may lookup one or more common abnormal flow rate graphs 304 in a database. The database may be static or dynamic. For example, the database may be updated by insertion of a memory device and/or remotely via a network. In addition, the system 10 may learn what abnormal flow rates are associated with selected normal flow rate and update its own database.

Next, the system 10 displays the abnormal flow rate graph(s) 304 on the same screen as the normal flow rate graph 302 (block 208). Preferably, the graphs are time-aligned as shown in FIG. 3. In an embodiment, the user may scroll through multiple abnormal flow rate graphs 304 using arrow buttons 312 while still viewing the normal flow rate graph 302.

Finally, the system also displays the actual flow rate graph 306 associated with the patient (block 210) and any alarms 308 (block 212) associated with the dialysis. Preferably, the actual flow rate graph 306 is time-aligned with the normal flow rate graph 302 and the abnormal flow rate graph(s) 304 as shown in the example of FIG. 3. In an embodiment, the user may scroll through multiple actual flow rate graphs 306 using arrow buttons 314 while still viewing the normal flow rate graph 302 and the abnormal flow rate graph(s) 304. For example, historical flow rate graphs may be viewed in this manner.

In the example illustrated in FIG. 3, at the point in time reached by the actual flow rate graph 306 (e.g., 7 minutes in to a 20 minute treatment), the actual flow rate graph 306 appears more similar to the abnormal flow rate graph 304 than it does to the normal flow rate graph 302 due to the steeper decline. Accordingly, this issue may be visually diagnosed as an occlusion. If the user was uncertain, the user may scroll through other possible abnormal flow rate graphs 304 using arrow buttons 312. In an alternate embodiment, the system 10 may offer diagnosis recommendations based on a mathematical comparison of the shape of the curves as well as indications of patient usage error such as drain bypasses.

In summary, persons of ordinary skill in the art will readily appreciate that methods and apparatus for displaying flow rate graphs and alarms on a dialysis system have been provided. The foregoing description has been presented for the purposes of illustration and description. It is not intended to be exhaustive or to limit the invention to the exemplary embodiments disclosed. Many modifications and variations are possible in light of the above teachings. It is intended that the scope of the invention be limited not by this detailed description of examples, but rather by the claims appended hereto.

The invention claimed is:

1. A method of displaying flow rate graphs and alarms on a dialysis system, the method comprising:
   prescribing a flow rate for a patient;
   selecting a normal flow rate graph based upon the prescribed flow rate;
   determining an abnormal flow rate graph associated with the selected normal flow rate graph, the abnormal flow rate graph representing an abnormal flow rate indicative of a problem in performing dialysis; and
   prompting visual diagnosis of an actual flow rate graph by simultaneously displaying the normal flow rate graph, the abnormal flow rate graph, the actual flow rate graph representing an actual flow rate measured during dialysis on the patient, and an alarm type, wherein each of the normal flow rate graph, the abnormal flow rate graph, and the actual flow rate graph are time-aligned with each other.

2. The method of claim 1, wherein the dialysis system is a peritoneal dialysis system.

3. The method of claim 1, wherein the dialysis system is a hemodialysis system.

4. The method of claim 1, wherein selecting the normal flow rate graph includes selecting a graph image.

5. The method of claim 4, wherein selecting the graph image includes selecting the graph image using a touch screen.

6. The method of claim 1, wherein selecting the normal flow rate graph includes selecting a graph name.

7. The method of claim 6, wherein selecting the graph name includes selecting the graph name using a touch screen.

8. The method of claim 1, wherein determining the abnormal flow rate graph associated with the selected normal flow rate graph includes a database lookup.

9. The method of claim 1, further comprising allowing the user to scroll through a plurality of abnormal flow rate graphs while still displaying the normal flow rate graph.

10. The method of claim 1, further comprising allowing the user to scroll through a plurality of abnormal flow rate graphs while still displaying the actual flow rate graph.

11. The method of claim 1, which further includes (i) performing a mathematical comparison of at least two of (a) the normal flow rate graph, (b) the abnormal flow rate graph, or (c) the actual flow rate graph, and (ii) displaying a diagnosis based upon the mathematical comparison.

12. The method of claim 1, wherein the problem indicated by the abnormal flow rate is one of: (i) a catheter occlusion, (ii) a drain problem, (iii) an occurrence of peritonitis, or (iv) an occurrence of constipation.

13. The method of claim 1, wherein the normal flow rate graph, the abnormal flow rate graph and the actual flow rate graph are displayed on three different sets of axes.

14. An apparatus for displaying flow rate graphs and alarms on a dialysis system, the system comprising:
   a processor;
   an input device operatively coupled to the processor;
   an output device operatively coupled to the processor; and
   a memory device operatively coupled to the processor, the memory device storing a software program to cause the processor to:
      receive a prescribed flow rate for a patient;
      receive a selection of a normal flow rate graph based upon the prescribed flow rate;
      determine an abnormal flow rate graph associated with the selected normal flow rate graph, the abnormal flow rate graph representing an abnormal flow rate indicative of a problem in performing dialysis; and
      simultaneously display the normal flow rate graph, the abnormal flow rate graph, an actual flow rate graph representing an actual flow rate measured during dialysis on the patient, and an alarm type, wherein each of the normal flow rate graph, the abnormal flow rate graph, and the actual flow rate graph are time-aligned with each other.

15. The apparatus of claim 14, wherein the dialysis system is a peritoneal dialysis system.

16. The apparatus of claim 14, wherein the dialysis system is a hemodialysis system.

17. The apparatus of claim 14 wherein receiving the normal flow rate graph selection includes receiving a graph image selection.

18. The apparatus of claim 17, wherein receiving the graph image selection includes receiving the graph image selection via a touch screen.

19. The apparatus of claim 14 wherein receiving the normal flow rate graph selection includes receiving a graph name selection.

20. The apparatus of claim 19, wherein receiving the graph name selection includes receiving the graph name selection via a touch screen.

21. The apparatus of claim 14, wherein determining the abnormal flow rate graph associated with the selected normal flow rate graph includes a database lookup.

22. The apparatus of claim 14, wherein the software program causes the processor to allow user scrolling through a plurality of abnormal flow rate graphs while still displaying the normal flow rate graph.

23. The apparatus of claim 14, wherein the software program causes the processor to allow user scrolling through a plurality of abnormal flow rate graphs while still displaying the actual flow rate graph.

24. The apparatus of claim 14, which further includes (i) performing a mathematical comparison of at least two of (a) the normal flow rate graph, (b) the abnormal flow rate graph, or (c) the actual flow rate graph, and (ii) displaying a diagnosis based upon the mathematical comparison.

25. The apparatus of claim 14, wherein the problem indicated by the abnormal flow rate is one of: (i) a catheter occlusion, (ii) a drain problem, (iii) an occurrence of peritonitis, or (iv) an occurrence of constipation.

26. The apparatus of claim 14, wherein the normal flow rate graph, the abnormal flow rate graph and the actual flow rate graph are displayed on three different sets of axes.

27. A memory device storing software instructions to cause a processor in a dialysis system to:
   receive a prescribed flow rate for a patient;
   receive a selection of a normal flow rate graph based upon the prescribed flow rate;
   determine an abnormal flow rate graph associated with the selected normal flow rate graph, the abnormal flow rate graph representing an abnormal flow rate indicative of a problem in performing dialysis; and
   simultaneously display the normal flow rate graph, the abnormal flow rate graph, an actual flow rate graph representing an actual flow rate measured during dialysis on the patient, and an alarm type, wherein each of the normal flow rate graph, the abnormal flow rate graph, and the actual flow rate graph are time-aligned with each other.

28. The memory device of claim 27, wherein the dialysis system is a peritoneal dialysis system.

29. The memory device of claim 27 wherein the dialysis system is a hemodialysis system.

30. The memory device of claim 27 wherein receiving the normal flow rate graph selection includes receiving a graph image selection.

31. The memory device of claim 30, wherein receiving the graph image selection includes receiving the graph image selection via a touch screen.

32. The memory device of claim 27 wherein receiving the normal flow rate graph selection includes receiving a graph name selection.

33. The memory device of claim 32, wherein receiving the graph name selection includes receiving the graph name selection via a touch screen.

34. The memory device of claim 27, wherein determining the abnormal flow rate graph associated with the selected normal flow rate graph includes a database lookup.

35. The memory device of claim 27, wherein the software instructions cause the processor to allow user scrolling through a plurality of abnormal flow rate graphs while still displaying the normal flow rate graph.

36. The memory device of claim 27, wherein the software instructions cause the processor to allow user scrolling through a plurality of abnormal flow rate graphs while still displaying the actual flow rate graph.

37. The memory device of claim 27, which further includes (i) performing a mathematical comparison of at least two of (a) the normal flow rate graph, (b) the abnormal flow rate graph, or (c) the actual flow rate graph, and (ii) displaying a diagnosis based upon the mathematical comparison.

38. The memory device of claim 27, wherein the problem indicated by the abnormal flow rate is one of: (i) a catheter occlusion, (ii) a drain problem, (iii) an occurrence of peritonitis, or (iv) an occurrence of constipation.

39. The memory device of claim 27, wherein the normal flow rate graph, the abnormal flow rate graph and the actual flow rate graph are displayed on three different sets of axes.

\* \* \* \* \*